United States Patent
Trinschek et al.

(10) Patent No.: US 11,447,825 B2
(45) Date of Patent: Sep. 20, 2022

(54) IN-VITRO METHODS FOR THE DETECTION OF AUTOIMMUNE DISEASES OR CONDITIONS

(71) Applicant: Universitätsmedizin der Johannes Gutenberg-Universität Mainz, Mainz (DE)

(72) Inventors: Bettina Trinschek, Hochheim (DE); Kazuki Satoh, Tokyo (JP); Helmut Jonuleit, Rüsselsheim (DE)

(73) Assignee: Universitätsmedizin der Johannes Gutenberg-Universität Mainz, Mainz (DE)

( * ) Notice: Subject to any disclaimer, the term of this patent is extended or adjusted under 35 U.S.C. 154(b) by 173 days.

(21) Appl. No.: 15/747,380

(22) PCT Filed: Aug. 9, 2016

(86) PCT No.: PCT/EP2016/068949
§ 371 (c)(1),
(2) Date: Jan. 24, 2018

(87) PCT Pub. No.: WO2017/025533
PCT Pub. Date: Feb. 16, 2017

(65) Prior Publication Data
US 2018/0216186 A1 Aug. 2, 2018

(30) Foreign Application Priority Data
Aug. 11, 2015 (EP) .................... 15180501

(51) Int. Cl.
*C12Q 1/6883* (2018.01)
*G01N 33/569* (2006.01)
*G01N 33/564* (2006.01)

(52) U.S. Cl.
CPC ......... *C12Q 1/6883* (2013.01); *G01N 33/564* (2013.01); *G01N 33/56972* (2013.01); *C12Q 2600/106* (2013.01); *C12Q 2600/112* (2013.01); *C12Q 2600/158* (2013.01); *G01N 2333/70514* (2013.01)

(58) Field of Classification Search
None
See application file for complete search history.

(56) References Cited

U.S. PATENT DOCUMENTS

2013/0195919 A1 8/2013 Von Andrian

FOREIGN PATENT DOCUMENTS

CN 102146474 3/2013

OTHER PUBLICATIONS

Kakoola et al., 2014, Results in Immunol. vol 4: 30-45.*
Wang et al., 2014, J. Food Sci. vol. 79: H1823-H1831.*
Beier et al., Epub Feb. 13, 2015, FASEB J, vol. 29:2315-2326.*
Byersdorfer et al., 2013, Blood. vol. 122: 3230-3237.*
Yang et al., 2008, Immunity vol. 28: 29-39.*
Progress in Autoimmune Disease Reseach, 2005, pp. 1-126.*
Kunz et al., 2009, Med. Inflammation, pp. 1-20.*
Teague et al., 1999, PNAS, vol. 96: 12691-1296.*
Satoh et al., 2006, J. Neur. 108-118.*
Baecher-Allen et al, "Suppressor T cells in human diseases", J. Exp. Med., vol. 200:3, pp. 273-276, (Aug. 2004).
Pollizzi, K. et al, "Integrating canonical and metabolic signalling programmes in the regulation of T cell responses", The Journal of Immunology, vol. 14:7, pp. 435-446, XP055240139, (Jun. 25, 2014).
Beavis, P. et al, "Resistance to regulatory T cell-mediated suppression in rheumatoid arthritis can e bypassed by eptopic foxp3 expression in pathogenic synovial T cells", Proceedings of the National Academy of Science, vol. 108:40, p. 16717-16722, XP055239895, (Sep. 16, 2011).
Josefowicz, S. et al, "Regulatory T cells: mechanisms of differentiation and function", Annual Review of Immunology, vol. 30:1, pp. 531-564, XP055240580, (Apr. 23, 2012).
Sakaguchi, S. et al, "Regulatory T cells: how do they suppress immune responses?", International Immunology, Immunology in Japan, vol. 21:10, pp. 1105-1111, (Aug. 2009).
Thornton, A. et al, "CD4+CD25+ Immunoregulatory T cells suppress polyclonal T cell activation in vitro by inhibiting Interleukin 2production", The Journal of Experimental Medicine, vol. 188:2, pp. 287-296, (Jul. 1998).
Powrie, F. et al, "Phenotypically distinct subsets of CD4+ T cells induce or protect from chronic intestinal inflammation in C. B-17 scid mice", International Immunology, vol. 5:11, pp. 1461-1471, (Nov. 1993).

(Continued)

*Primary Examiner* — Amy E Juedes (74) *Attorney, Agent, or Firm* — McHale & Slavin, P.A.

(57) ABSTRACT

A method for the detection of impaired responsiveness of CD4+ T-cells to regulatory T-cells (Treg), Treg resistance, by measuring the expression levels of peroxisome proliferator-activated receptor gamma coactivator 1-alpha, PPARGC1A (PGC-1α) in activated CD4+ T-cells, in particular in patients suffering from relapsing remitting multiple sclerosis. The invention relates to an in vitro screening method for the detection of an autoimmune disease or a condition, comprising the steps of generating a functional gene expression profile by measuring the expression levels of peroxisome proliferator-activated receptor gamma coactivator 1-alpha, PPARGC1A (PGC-1α) in Treg-resistant CD4+ T-cells from patients suffering of an autoimmune disease or condition, and comparing the obtained gene expression profile with the expression profile from Treg-sensitive CD4+ T-cells from healthy controls. PCG-1α or an upstream regulator of Treg-resistant T-cells HNF4A, Hdac, RORA, ESRRA, LPIN1 can be used in a screening system for the detection of impaired responsiveness of CD4+ T-cells to Treg.

4 Claims, 5 Drawing Sheets

(56) References Cited

OTHER PUBLICATIONS

Kelchtermans, H. et al, "Defective CD4+CD25+ regulatory T cell functioning in collagen-induced arthritis: an important factor in pathogenesis, counter-regulated by endogenous IFN-γ", Arthritis Res. Ther., vol. 7, pp. R402-R415, (2005).

Schneider, A. et al, "In active relapsing-remitting multiple sclerosis, effector T cell resistance to adaptive T(regs) involves IL-6-mediated signaling", Sci. Transl. Med, vol. 5:170, p. 170ra15, (Jan. 2013).

Belkaid, Y. et al, "CD4+CD25+ regulatory T cells control Leishmana major persistence and immunity", Nature, vol. 20, pp. 502-507, (Dec. 2002).

Zozulya, A. et al., "The role of regulatory T cells in multiple sclerosis", Internet article: http://www.nature.com/clinicalpractice, pp. 1-15, (Jun. 2008).

Goverman, J., "Autoimmune T cell responses in the central nervous system", Nat. Rev. Immunol., vol. 9:6, pp. 1-28, (Jun. 2009).

Jonuleit, H. et al, "Identification and functional characterization of human CD4+CD25+ T cells with regulatory properties isolated from peripheral blood", J. Exp. Med., vol. 193:11, pp. 1285-1294, (Jun. 2001).

Jonuleit, H. et al, "Infectious tolerance: human CD25+ regulatory T cells convey suppressor sctivity to conventional CD4+ T cell helpers", J. Exp. Med, vol. 196:2, pp. 255-260, (Jul. 2002).

Costantino, C. et al., "Multiple sclerosis and regulatory T cells", J. Clin. Immunol., vol. 28:6, pp. 697-706, (Nov. 2008).

Stassen, M. et al, "Human CD25+ regulatory T cells: two subsets defined by the integrins alpha4beta7 or alpha4beta1 confer distinct suppressive properties upon CD4+ T cell helpers", Eur. J. Immunol., vol. 34, pp. 1303-1311, (2004).

Vladic, A. et al, "Cerebrospinal fluid and serum protein levels of tumour necrosis factor-alpha (TFN-alpha) Interleukin-6 (IL-6) and soluble interleukin-6 receptor (sIL-6R gp80) in multiple sclerosis patients", Cytokine, vol. 20:2, pp. 86-89, (Oct. 2002).

Haas, J. et al, "Reduced suppressive effect of CD4+CD25+ high regulatory T cells on the T cell immune response against myelin oligodendrocyte glycoprotein in patients with multiple sclerosis", Eur. J. Immunol., vol. 35, pp. 3343-3352, (2005).

Ferrante, P. et al, "Cytokine production and surface marker expression in acute and stable multiple sclerosis: altered IL-12 production and augmented signaling lymphocytes in acute multiple sclerosis1", The J. of Immunol., vol. 160, pp. 1514-1521, (1998).

McGeachy, M. et al, "Natural recovery and protection from autoimmune encephalomyelitis: contribution of CD4 +CD25+ regulatory cells within the central nervous system", J. Immunol., vol. 175:5), pp. 3025-3032, (Sep. 2005).

Katsavos, S. et al, "Biomarkers in multiple sclerosis: an up-to-date Overview", Multiple Sclerosis International, vol. 2013, Article ID 340508, pp. 1-20, (2013).

Trinschek, B. et al, "Kinetics of IL-6 production defines T effector cell responsiveness to regulatory T cells in multiple sclerosis", PLOS ONE, vol. 8:10, e77634, pp. 1-14, (Oct. 2013).

Weiner, H., "The challenge of multiple sclerosis: how do we cure a chronic heterogeneous disease?", American Neurological Association, vol. 65, pp. 239-248, (2009).

\* cited by examiner

IN-VITRO METHODS FOR THE DETECTION OF AUTOIMMUNE DISEASES OR CONDITIONS

CROSS REFERENCE TO RELATED APPLICATIONS

This is a national stage filing in accordance with 35 U.S.C. § 371 of PCT/EP2016/068949, filed Aug. 9, 2016, which claims the benefit of the priority of European Patent Application No. 15180501.7, filed Aug. 11, 2015, the contents of each are incorporated herein by reference.

FIELD OF THE INVENTION

Naturally occurring CD4+ CD25+ regulatory T-cells (Treg) represent a unique T-cell lineage that is endowed with the ability to actively suppress immune responses. Treg represent less than 2% of all peripheral T-cells in healthy individuals (Jonuleit H. et al. Identification and functional characterisation of human CD4+ CD25+ T-cells with regulatory properties isolated from peripheral blood. J Exp Med. 2001; 193:1285-1294).

DESCRIPTION OF THE BACKGROUND ART

As immune modulators, Treg play a critical role in the maintenance of a peripheral immunologic tolerance by suppressing the activation of other immune cells and conferring regulatory properties upon suppressed T effector cells (Jonuleit et al., Infectious tolerance human CD25(+) regulatory T-cells convey suppressor activity to conventional CD4(+) T helper cells. *J. Exp Med.* 2002, 196.255-260; Stassen M. et al. Human CD25+ regulatory T-cells: two subsets defined by the integrins alpha 4 beta 7 or alpha 4 beta 1 confer distinct suppressive properties upon CD4+ T helper cells. *Eur J Immunol.* 2004; 34:1303-1311). An impaired responsiveness of CD4+ T-cells to regulatory T-cells (Treg) is also known as Treg resistance. Treg resistance is detectible in a number of inflammatory and non-inflammatory autoimmune diseases. While the suppressive function of Treg depends on the activation, once activated, Treg suppress other immune cells in a non-specific manner resulting in a broad and systemic immunoregulatory effect (Thornton et al., CD4+ CD25+ immunoregulatory T-cells suppress polyclonal T cell activation in vitro by inhibiting interleukin 2 production. *J Exp Med.* 1998, 188:287-296). The activation of autoreactive T-cells is controlled by regulatory T-cells (Treg) under physiological conditions (Jonuleit et al., 2001. Identification and functional characterization of human CD4(+)CD25(+) T-cells with regulatory properties isolated from peripheral blood. *J Exp. Med.* 193:1285-1924; Josefowicz et al, 2012. Regulatory T-cells: mechanisms of differentiation and function. *Annual review of immunology* 30:531-564; Sakaguchi et al., 2009. Regulatory T-cells: how do they suppress immune responses? *International immunology* 21:1105-1111). Due to their unique function to regulate innate and adaptive immune responses, Treg have become a major subject in immunological research. As such, Treg play a major role in a number of autoimmune conditions or diseases such as rheumatoid arthritis, rheumatic fever, systemic lupus erythematosus (SLE), ulcerative colitis, Crohn's disease, autoimmune inflammatory bowel disease, diabetes type I, multiple sclerosis (MS), myasthenia gravis, psoriasis, pemphigus vulgaris, pemphigoid (Kelchtermans et al., Defective CD4+ CD25+ regulatory T cell functioning in collagen-induced arthritis: an important factor in pathogenesis, counter-regulated by endogenous IFN-gamma. Arthr res ther., 2005, 7:r402-r415; 14. Mcgeachy et al., Natural recovery and protection from autoimmune encephalomyelitis: contribution of CD4+ CD25+ regulatory cells within the central nervous system. J Immunol. 205, 175:3025-3032 15; Powrie et al., Phenotypically distinct subsets of CD4+ t cells induce or protect from chronic intestinal inflammation in C. B-17 scid mice, 1993, Int. Immunol. 5:1461-1471; Belkaid et al., CD4+ CD25+ regulatory T cells control Leishmania major persistence and immunity. Nature 2002, 420:502-507).

Among these diseases multiple sclerosis (MS) is difficult to treat because as a heterogeneous autoimmune disease only a small portion of patients respond to therapy. New therapeutic treatments are difficult to investigate, although the therapeutically success has been significantly improved in the recent years. It is known so far that Treg are functionally impaired in MS patients (Baecher-Allan and Hafler, 2004b. Suppressor T-cells in human diseases, *J Exp. Med.* 200:273-276; Costantino et al., 2008. Multiple sclerosis and regulatory T-cells. *J Clin Immunol* 28:697-706; Haas et al., 2005. Reduced suppressive effect of CD4+ CD25 high regulatory T-cells on the T-cell immune response against myelin oligodendrocyte glycoprotein in patients with multiple sclerosis. *European journal of immunology* 35:3343-3352; Schneider et al., 2013, "In active relapsing-remitting multiple sclerosis, effector T-cell resistance to adaptive T(regs) involves IL-6-mediated signalling", *Sci. Transl. Med.* 5:170ra115; Trinschek et al., 2013 Kinetics of IL-6 production defines T effector cell responsiveness to regulatory T-cells in multiple sclerosis. *PloS one* 8:e77634; Zozuyla and Siendl, 2008. The role of regulatory T-cells in multiple sclerosis. *Nat. Clin. Pract. Neurol.* 4:384-398). Due to this imbalance, autoreactive T-cells escape suppression by Treg and migrate through the blood brain barrier to attack the central nervous system (Goverman, 2009. Autoimmune T-cell responses in the central nervous system. *Nature reviews. Immunology* 9:393-407). The cytokine IL-6 plays a major role by inducing an enhanced PKB/c-Akt phosphorylation, upregulated IL-6R expression and in a positive feedback loop its own accelerated production (Trinschek et al., 2013. Kinetics of IL-6 production defines T-effector cell responsiveness to regulatory T-cells in multiple sclerosis. *PloS one* 8:e77634).

PPARGC1A is also known in context with the detection of type 2 diabetes mellitus, which according to CN 102 146 474 B can be detected by measuring the expression level of PPARGC1A in leukocytes.

However, by now it is not possible to distinguish between defective Treg and Treg-resistant T-cells in patients with autoimmunity. This differentiation is complicated by the fact that both T-cell populations do not differ in their expression of certain activation markers or their cytokine profiles (Ferrante et al., 1998. Cytokine production and surface marker expression in acute and stable multiple sclerosis: altered IL-12 production and augmented signaling lymphocytic activation molecule (SLAM)-expressing lymphocytes in acute multiple sclerosis. *Journal of Immunology* (Baltimore, Md.: 1950) 160:1514-1521; Vladic et al., 2002. Cerebrospinal fluid and serum protein levels of tumour necrosis factor-alpha (TNF-alpha) interleukin-6 (IL-6) and soluble interleukin-6 receptor (sIL-6R gp80) in multiple sclerosis patients. *Cytokine* 20:86-89). These barriers increased the demand for the identification of molecules that are associated with impaired T-cell function and that provide important insights in the understanding of T-cell-Treg interaction (Havla et al., 2015. [Immunotherapies for multiple sclerosis:

review and update]. *Der Internist* 56:432-445; Katsavos and Anagnostouli, 2013. Biomarkers in Multiple Sclerosis: An Up-to-Date Overview. *Multiple sclerosis international* 2013:340508; Weiner, 2009. The challenge of multiple sclerosis: how do we cure a chronic heterogeneous disease? *Annals of neurology* 65:239-248).

SUMMARY OF THE INVENTION

It is therefore the object of the present invention to provide new and improved methods that allow for the detection of impaired responsiveness of T-effector cells to regulatory T-cells (Treg), and the detection of inflammatory and non-inflammatory autoimmune conditions or diseases associated with Treg resistance.

This object is solved by the methods and the therein utilized biological marker molecules according to the present invention. Preferred embodiments are subject-matter of the dependent claims.

The present invention concerns methods for the detection of impaired responsiveness of CD4+ T-cells to regulatory T-cells (Treg), referred to as Treg resistance, by measuring the expression levels of peroxisome proliferator-activated receptor gamma co-activator 1-alpha, PPARGC1A (PGC-1α), or other upstream regulators of Treg-resistant T-cells in activated CD4+ T-cells.

The invention aims to identify biological molecules that allow the detection of Treg resistance in isolated human or animal cells or cell cultures. It is demonstrated by the inventors that Treg resistance is caused by increased IL-6 receptor expression, accelerated IL-6 production an enhanced phosphorylation of PKB/c-Akt. Functional genetic expression profiles of Treg-resistant CD4+ T-cells from patients suffering of an autoimmune disease were generated to identify potential biomarkers associated with Treg resistance. The expression profiles of Treg-activated T-cells, their proliferative capacity and the cytokine production do not differ between activated T-cells of patients suffering of an autoimmune disease and healthy individuals. The herein identified biomarkers are associated with Treg resistance and provide a diagnostic tool to monitor therapeutic success of a given treatment. As a consequence, autoimmune diseases can be personalized by addressing specific molecules leading to reduced side effects, thereby enhancing therapy efficiency and success. The herein identified biomarkers are closely linked to the IL-6 pathway, which plays a major role by inducing an enhanced PKB/c-Akt phosphorylation, up-regulated IL-6 R expression and in a positive feedback loop its own accelerated production.

The peroxisome proliferator-activated receptor gamma coactivator 1-alpha, PPARGC1A (PGC-1α) is one candidate that has been further investigated by the inventors and that fulfills all criteria of a biomarker for the detection of Treg resistance and hence the detection of an autoimmune condition or disease associated with Treg resistance. Patients with multiple sclerosis (MS) were compared with healthy individuals in a study that compares the expression profiles of PGC-1α in activated T-cells. Accordingly, effector T-cells from MS-patients show a strongly reduced expression level compared to T-cells from healthy individuals. Functional bioinformatic analyses were applied to identify a number of other biomarkers which are specific for MS and other autoimmune conditions, all of which are closely linked to T-cell function and Treg resistance. Similar to PGC-1α, the other upstream regulators of Treg-resistant T-cells HNF4A, Hdac, RORA, ESRRA, LPIN1 are also significantly upregulated in Treg-sensitive CD4+ and CD8+ T-cells of healthy individuals upon activation, but down-regulated in activated Treg-resistant T-cells of autoimmune patients, which makes them suitable candidates for detection of Treg resistance and/or autoimmune disorders.

Since T-cell susceptibility to Treg correlates with PGC-1α expression levels, the expression of PGC-1α is down-regulated in response to IL-6 as well as in activated T-cells of autoimmune patients and expression levels correlated with Treg-resistance. Since PGC-1α is down-regulated in autoimmune patients, a therapy could be directed to the up-regulation of PGC-1α in activated T-cells in order to improve susceptibility to Treg function.

The inventors further found that PGC-1α down-regulation is directly inducible by IL-6, thereby providing promising approaches for the development of new therapeutic strategies. IL-6 is known to be a pleiotropic cytokine that has a key function in immune responses and also contributes to development and maintaining of several autoimmune diseases (Malpass, 2013; Neurath and Finotto, 2001). PKB/c-Akt phosphorylation is accelerated by IL-6 synthesis, which is found in T-cells of arthritis and MS patients that render these cells insensitive to Treg control.

As part of the therapeutic approach, agonists that can up-regulate PGC-1α expression in activated T-cells of autoimmune patients can be identified. In the present invention, the effect of IFN-β has been demonstrated in T-cells isolated from MS patients in order to induce up-regulation of PGC-1α expression in these T-cells. PGC-1α expression levels can be nearly normalized upon IFN-β treatment, demonstrating that PGC-1α is also suitable as a marker for monitoring therapeutic treatment process. It was further found that the induction of PGC-1α expression prevents PKB/c-Akt phosphorylation and subsequently restored the sensitivity to Treg-mediated suppression even in presence of IL-6. Furthermore, IFN-β treatment induced a normalized expression profile of PGC-1α that was associated with the restauration of T-cell function, demonstrating that PGC-1α is a master regulator in the transmission of suppression by Treg.

The detection of Treg resistance is preferably carried out by comparing the expression levels of PGC-1α or any other of the identified biomarker molecules HNF4A, Hdac, RORA, ESRRA, LPIN1 with the respective biomarker expression levels of activated Treg-sensitive CD4+ T-cells, wherein a down-regulation of PGC-1α or any other of the mentioned biomarkers within activated Treg-resistant T-cells as compared to the activated Treg-sensitive CD4+ and CD8+ T-cells is indicative for Treg resistance. In the methods according to the present invention, up-regulation of PGC-1α or any other of the biomarkers is correlated with a responsiveness of Treg-sensitive CD4+ T-cells to Treg-mediated suppression. Further controls are available for Treg resistance since a down-regulation of PGC-1α is associated with an accelerated IL-6 production following T cell receptor (TCR) stimulation, enhanced phosphorylation of PKB/c-Akt and/or an increased IL-6 receptor (IL-6R) expression.

The present invention also concerns an in-vitro screening method for the detection of an inflammatory disease or an autoimmune condition, comprising the steps of generating a functional gene expression profile by measuring the expression levels of peroxisome proliferator-activated receptor gamma coactivator 1-alpha, PPARGC1A (PGC-1α) in Treg-resistant CD4+ T-cells from patients suffering of an autoimmune disease or condition, and comparing the obtained gene expression profile with the expression profile from Treg-sensitive CD4+ T-cells from healthy controls. In particular, the screening method of the invention allows an early detection of a number of autoimmune diseases such as multiple sclerosis when comparing the expression profiles in activated T-cells of MS patients compared to the expression profiles of healthy individuals. It is also acknowledged that the screening method of the invention can also be used for the detection of similar Treg-resistance-associated autoimmune diseases or conditions such as rheumatoid arthritis, rheumatic fever, systemic lupus erythematosus (SLE), ulcerative colitis, Crohn's disease, autoimmune inflammatory bowel disease, diabetes type I, myasthenia gravis, psoriasis, pemphigus vulgaris, pemphigoid. As further demonstrated, amelioration of T-cell function correlates with a normalization of PGC-1α expression, indicating that a restauration of Treg activity is a promising therapeutic approach for treatment of autoimmune disorders such as multiple sclerosis or any other of the mentioned autoimmune disorders. The transition from Treg-resistant affected T-cells to Treg-sensitive affected T-cells correlates with the expression levels of PGC-1α, or any other of the biomarker molecules such as HNF4A, Hdac, RORA, ESRRA, LPIN1. In addition, IL-6 expression levels increase significantly in activated T-cells from MS patients in which PGC-1α is down-regulated. On the other side, IL-6R expression is significantly reduced and PGC-1α is up-regulated in activated T-cells of healthy individuals. As mentioned before, down-regulation of PGC-1α in activated MS T-cells is linked to an enhanced PKB/c-Akt phosphorylation and unresponsiveness of T-cells to Treg mediated suppression. On the other hand, induction of PGC-1α expression was sufficient to prevent PKB/c-Akt phosphorylation and subsequently restored their sensitivity to Treg-mediated suppression even in the presence of IL-6.

The following examples will demonstrate the invention in more detail.

EXAMPLES

Advanced Gene Profiling of Treg-Resistant CD4+ T-Cells from MS Patients

Figure 1:
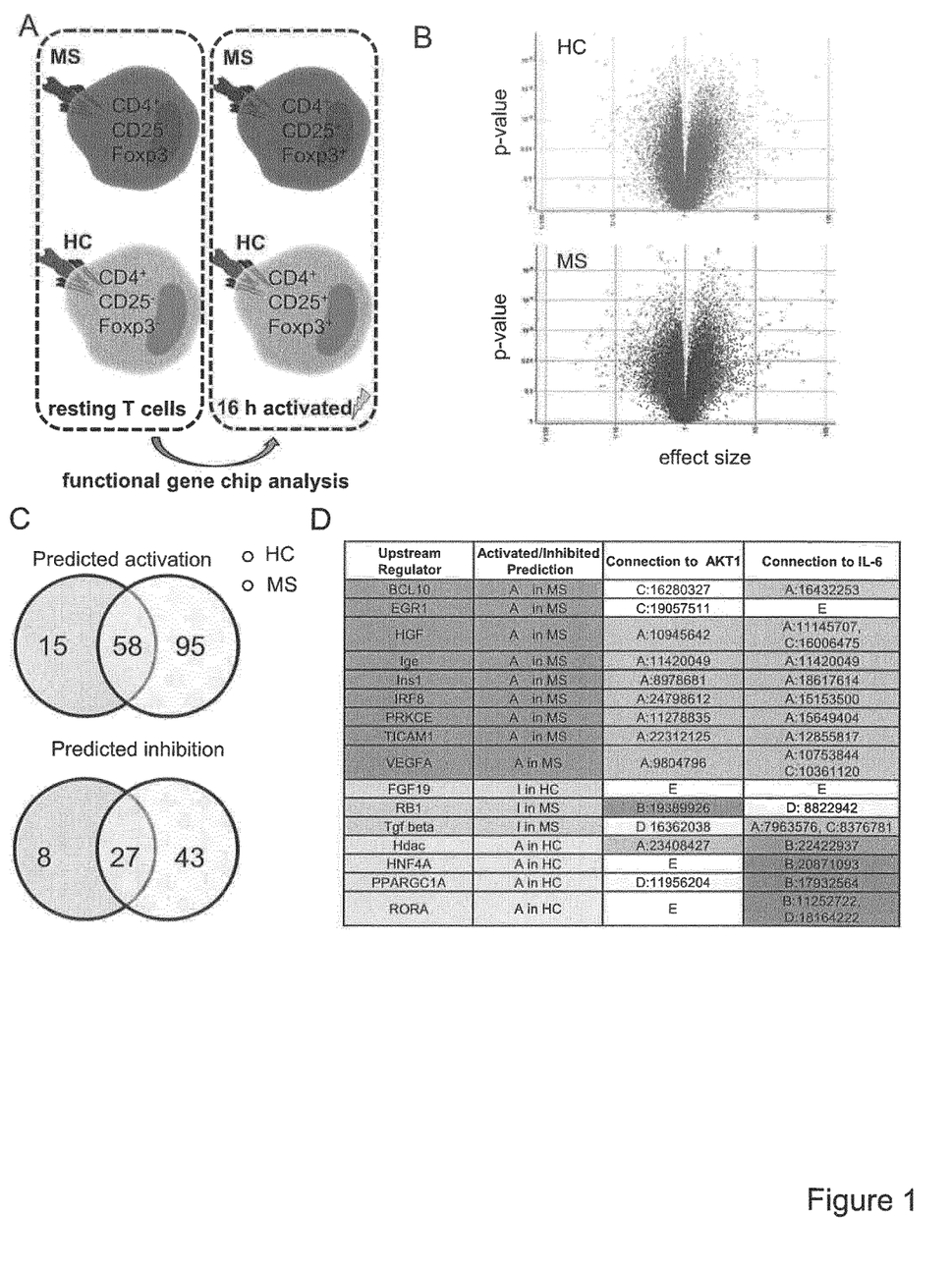
FIG. 1: Functional gene chip analysis identified 16 upstream regulators of Treg-resistant MS T-cells compared to Treg-sensitive T-cells of HC.

Since T cell activation processes are transcriptionally regulated, the inventors postulated that Treg resistance of MS T-cells is reflected by specific transcriptional changes in the gene expression profile. The inventors therefore analysed expression profiles of TCR stimulation-responsive genes of Treg-resistant MS CD4+ T-cells compared to Treg-sensitive HC (healthy controls) CD4+ T-cells (FIG. 1A). A number of 3,512 stimulatory response genes were identified in MS and 2,472 genes in HC T-cells with an altered expression upon stimulation (FIG. 1B). Subsequently, advanced bioinformatic analysis of upstream regulators was performed with data sets representing these differently regulated genes. It was the aim to determine hereby upstream regulators specifically activated or inhibited in T-cells of MS patients or HC (FIG. 1C). Additionally, to further curtail the group of upstream regulators, molecules with a high stringency and molecules that have functional association with the IL-6/c-Akt signalling pathway were depicted (FIG. 1D). These parameters reduced the group of target upstream regulators to 16 genes that should be functionally involved in Treg resistance.

Figure 2:
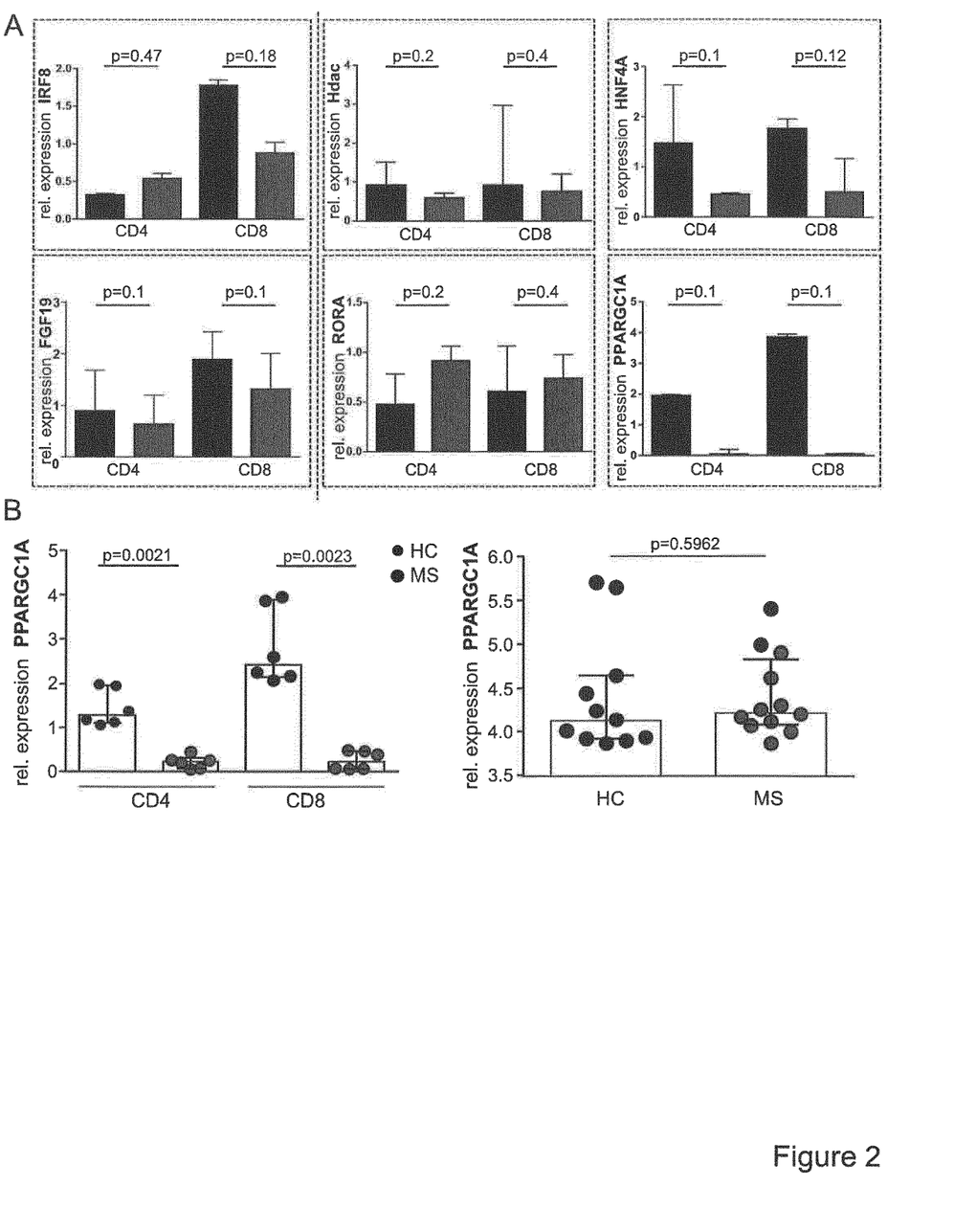
FIG. 2: qRT-PCR identifies PGC-1α as a potential molecule linked to Treg-resistance of MS T-cells.

PGC-1α is Strongly Up Regulated in TC of HC Upon Stimulation whereas it is Down Regulated MS T-Cells To investigate whether the molecules predicted to be associated with Treg resistance and IL-6 signalling are also differentially regulated itself, the inventors performed qRT-PCR of identified upstream regulators in CD4+ and CD8+ T-cells from MS patients and HC. Notably, the in silico predicted molecules HNF4A, Hdac and PPARGC1A (FIG. 2A) indeed are regulated itself as predicted by the bioinformatic analysis for its upstream regulators, whereas mRNA expression of IRF8, FGF19 and RORA did not alter. Strongest difference was found in PPARGC1A and further analyses revealed that expression of PPARGC1A was significantly up regulated in Treg-sensitive CD4+ and CD8+ T-cells of HC upon activation but down regulated in activated Treg-resistant T-cells of MS patients (FIG. 2B, left). Interestingly, the differential regulation is directly dependent on the activation state, since relative expression of resting T-cells in MS patients and HC is comparably expressed (FIG. 2B, right). PPARGC1A (peroxisome proliferator-activated receptor gamma coactivator 1-alpha) or short PGC-1α is known as a transcriptional coactivator that regulates genes involved in energy metabolism and was suggested to be a master integrator of external signals (Austin and St-Pierre, 2012; Wu et al., 1999). PGC-1α expression is connected to PKB/c-Akt and IL-6 signalling (Handschin et al., 2007; Romanino et al., 2011) further corroborating the bioinformatics prediction that this molecule represents a promising candidate for dysfunctional T-cells in MS patients.

IL-6 Blocks Upregulation of PGC-1α in Activated T-Cells

Figure 3:
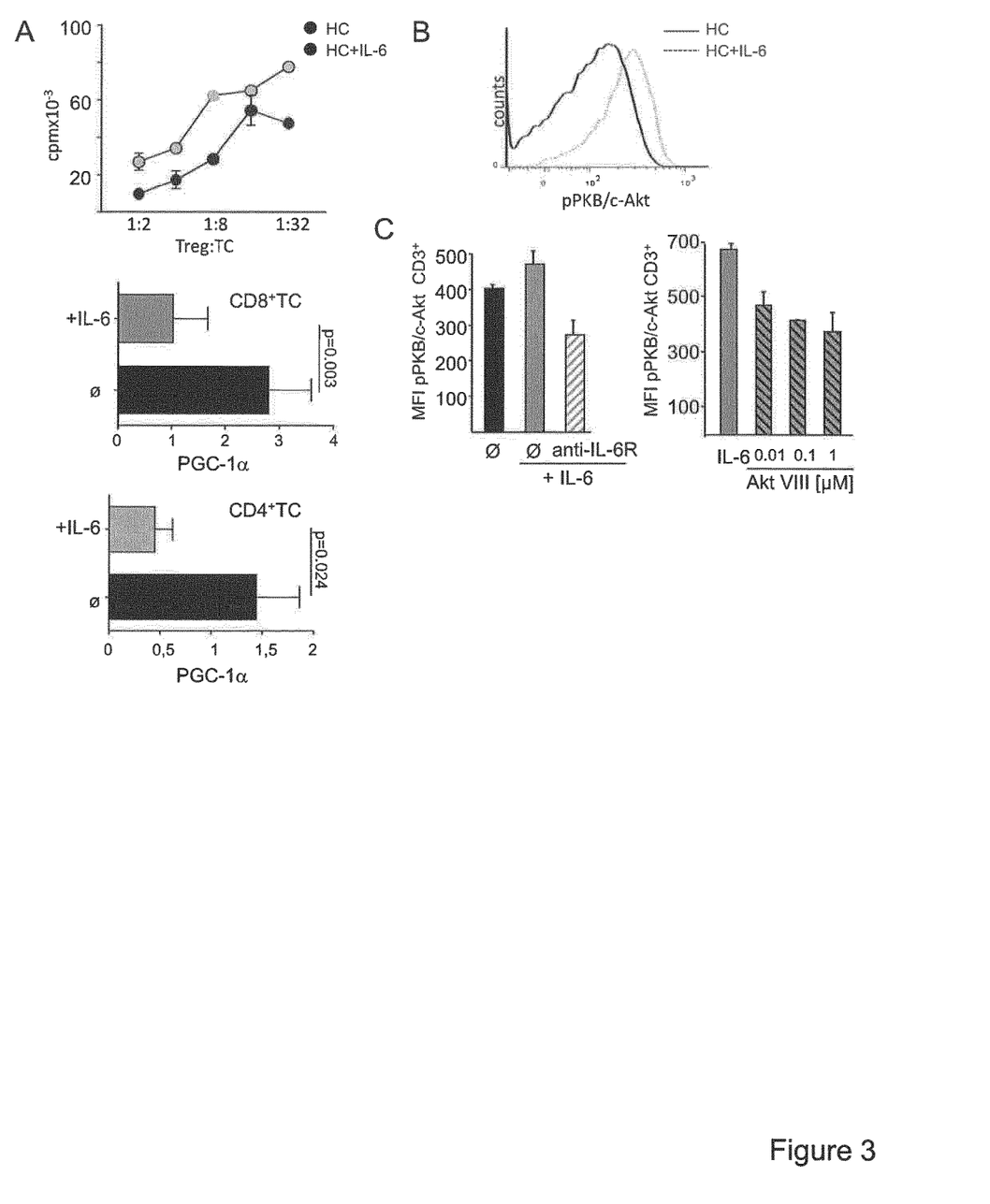
FIG. 3: IL-6 induces down regulation of PGC-1α in activated T-cells and thereby mediates Treg resistance.

To further investigate the role of IL-6 signalling in the regulation of PGC-1α and Treg resistance the inventors stimulated Treg-sensitive T-cells from HC alone or together with Treg in presence or absence of IL-6. Indeed, supplementation of IL-6 in suppressor cocultures prevented efficient control of T-cells by Treg (FIG. 3A). Concomitantly, addition of exogenous IL-6 prevented the upregulation of PGC-1α in activated CD8+ T-cells and even down regulated PGC-1α expression in activated CD4+ T-cells (FIG. 3A) both associated with an enhanced phosphorylation of PKB/c-Akt in these T-cells (FIG. 3B). Otherwise, anti-IL-6R mAb or the c-Akt inhibitor VIII inhibited phosphorylation of PKB/c-Akt (FIG. 3C) and consequently restored IL-6-induced Treg resistance. These results show that PGC-1α expression is strictly associated with Treg resistance and its regulation is modulated by IL-6.

Figure 4:
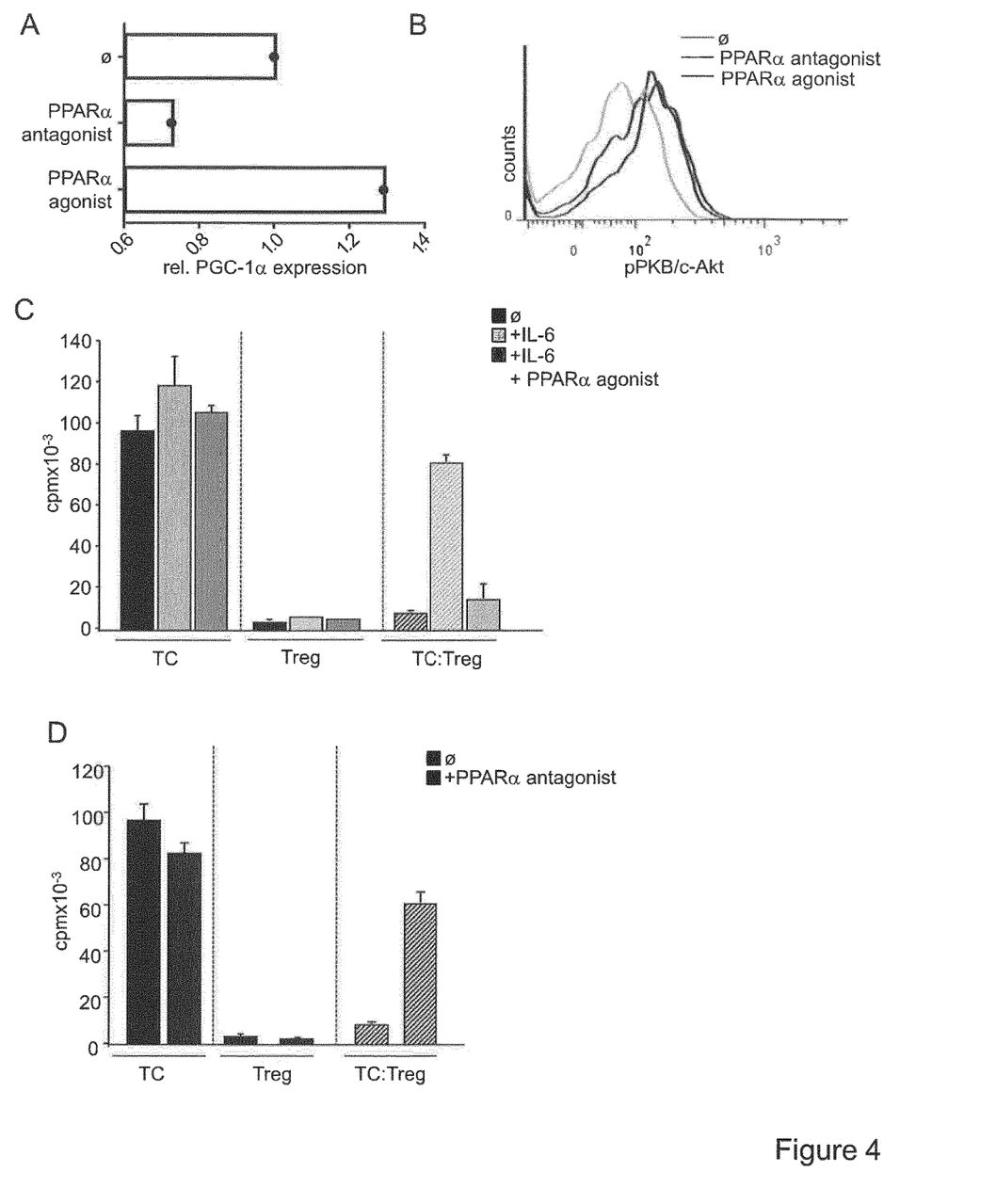
FIG. 4: Presence of PPARα agonists in cocultures induces PGC-1α upregulation and thereby restores T cell sensitivity also in presence of IL-6.

Upregulation of PGC-1α in T-Cells Prevents PKB/c-Akt Activation and Strictly Correlates with Their Responsiveness to Treg-Mediated Suppression In order to evaluate our hypothesis that PGC-1α upregulation in T-cells positively correlate with their sensitivity to Treg-mediated suppression, agonists and antagonists of peroxisome proliferator-activated receptor alpha (PPARα) were used. Activation of PPARα is necessary for mitochondrial biogenesis mediated by PGC-1α (Finck et al., 2006). Presence of PPARα agonist enhanced PGC-1α expression and simultaneously reduced PKB/c-Akt phosphorylation in T-cells. Incubation with the PPARα antagonist resulted in the expected opposite results (FIGS. 4A and B) without inducing toxicity (Supplemental FIG. 4). To investigate the functional consequence of PGC-1α modulation on the sensitivity of T-cells for Treg-mediated suppression, the modifiers in classical suppressor assays were used. In absence of Treg both PPARα modifiers, neither agonist nor antagonist, did not influence the T-cell proliferation significantly. However, addition of the agonist restored Treg-mediated suppression in cocultures even in presence of exogenous IL-6 (FIG. 4C). Otherwise, Treg resistance could be induced solely by administration of PPARα antagonist (FIG. 4D), demonstrating the importance of PGC-1α upregulation in T-cells for their susceptibility to Treg-mediated suppression.

Figure 5:
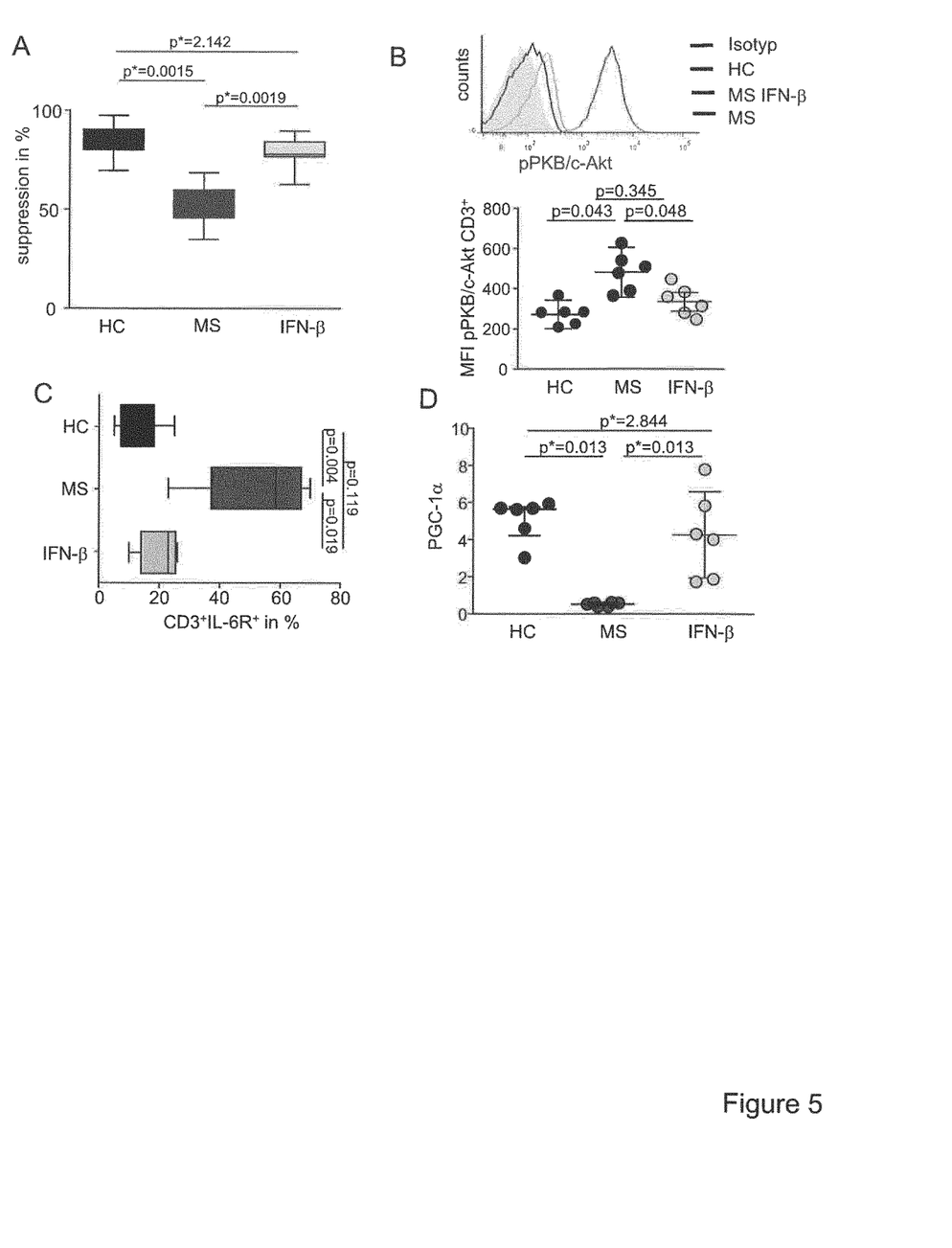
FIG. 5: Treg resistance of T-cells from MS patients is ameliorated after IFN-β therapy and correlated with upregulation of PGC-1α.

IFN-β Therapy Normalizes PGC-1α Expression and Restores Treg Responsiveness in T-Cells of MS Patients IFN-β is one standard therapy in the treatment of relapsing remitting MS but the mechanisms by which IFN-β exerts its effects are incompletely understood (Dubois et al., 2003). The inventors analysed if IFN-β therapy ameliorates T cell function of MS patients also with regard to Treg control. Here, it was found that a four month treatment with IFN-β restored sensitivity of peripheral T-cells to Treg-mediated suppression nearly to a level of T-cells from HC (FIG. 5A). This restored susceptibility to suppression correlated with a reduced PKB/c-Akt phosphorylation (FIG. 5B) and decreased IL-6R expression (FIG. 5C). To determine if restored T-cell responsiveness correlated with normalization of PGC-1α, PGC-1α mRNA expression was analysed in T-cells of MS patients with or without IFN-β therapy. Whereas PGC-1α was strongly down regulated after activation in therapy-naïve MS patients (FIG. 5D), a significant up-regulation of PGC-1α in patients that underwent IFN-β treatment comparable to the expression in activated T-cells from HC was found, demonstrating the potential of PGC-1α as a diagnostic tool for the prediction of therapeutic success.

The herein presented data demonstrate that PGC-1α is a suitable biomarker molecule, which is a T-cell specific and that correlates directly with T-cell susceptibility to Treg. Expression of PGC-1α is down-regulated in response to IL-6 in activated T-cells of MS patients and low levels of PGC-1α correlate with Treg resistance. Therapy-induced up-regulation of PGC-1α can be used for their proofed susceptibility to Treg function. Therefore, down-regulation of PGC-1α expression in peripheral T-cells is indicative for Treg resistance, which allows to identify Treg resistance-associated autoimmune conditions or disorders. It is also demonstrated that PGC-1α down-regulation is directly inducible by IL-6, which allows the development of new therapeutic strategies. On the other hand, phosphorylation of PKB/c-Akt prevents the recruitment of PGC-1α to the cognate promoters, impairing its ability to promote gluconeogenesis and fatty acid oxidation in diabetes patients. Up-regulation of PGC-1α by agonists, on the other hand, limited the phosphorylation of PKB/c-Akt, leading to T-cell sensitivity also in the presence of IL-6. IFN-β significantly improves the immune-regulation of auto-aggressive T-cells in MS patients by dampening signal transduction via the IL-6 pathway, thus restoring their sensitivity for Treg-mediated suppression. Amelioration of T-cell function correlates with a normalization of PGC-1α expression nearly to the level of healthy individuals, demonstrating that PGC-1α is a suitable marker for monitoring therapeutic approaches.

The results also provide strong evidence that advanced bioinformatic analysis is beneficial to discover molecules that are linked to dysregulated T-cell function. Down-regulation of PGC-1α in activated MS T-cells was linked to enhanced PKB/c-Akt phosphorylation and unresponsiveness of T-cells to Treg-mediated suppression. On the other hand, induction of PGC-1α expression was sufficient to prevent PKB/c-Akt phosphorylation and subsequently restored their sensitivity to Treg-mediated suppression even in the presence of IL-6. Furthermore, IFN-β treatment induced a normalized expression profile of PGC-1α that was associated with the restoration of T-cell function, demonstrating that PGC-1α is a master regulator in the transmission of suppression by Treg.

Methods

Patients and Healthy Controls 85 patients with a relapsing-remitting course (RRMS, age 18 to 64 years) and 4 patients with a clinically isolated syndrome (CIS, age 22 to 53) all fulfilling the revised McDonald criteria for multiple sclerosis were included in this study. 31 patients were treated for at least 4 month with IFN-β. 58 patients had not received previous treatment or immunosuppressive agents six months before time point of analysis and were clinically stable. PBMC from healthy controls served as controls. PBMC were isolated within 12 h after blood collection and were used directly in in vitro experiments. Blood was kept at room temperature before PBMC enrichment. According to the principles expressed in the Helsinki Declaration and to the ethics committee-approved protocols patients provided written informed consent before participating in this study.

Microarray Analysis

Total RNA was extracted and purified from T-cells using QIAshredder, RNeasy Mini kit, and RNase-Free DNase Set (QIAGEN) according to manufacturer's instructions. The integrity of RNA was verified with BioAnalyzer (Agilent). Complimentary DNA (cDNA) was synthesized from 100 ng of total RNA using Ambion WT Expression Kit (Life Technologies). Subsequently, cDNA was fragmented and biotinylated using gene chip WT Terminal Labelling and control kit (Affymetrix). Biotinylated cDNA fragment was hybridized to the gene chip Human Transcriptome Array 2.0, and then microarray was washed and stained with Fluidics Station 450 (Affymetrix) using gene chip Hybridization, Wash and Stain Kit (Affymetrix). The gene chip was then analysed with the gene chip Scanner 3000 (Affymetrix). Fluorescent signals corresponding to the intensity of hybridization intensity were normalized using the Robust Multichip Average method (RMA) from the Expression Console Software (Affymetrix). The inventors screened out gene probes which showed transcriptional differences more than 2-fold change in the median of three individuals by a polyclonal stimulation (Welch's t-test: $P<0.05$). Then, datasets representing differentially expressed genes were applied into the Ingenuity Pathways Analysis (IPA). The activation z-score was used for prediction of functional and transcriptional regulation in Upstream Analysis. The z-score is calculated from expression profiles in the gene probes belonging to each pathway, using the integrated information derived from experimentally observed transcriptionally altered events, compiled in the Ingenuity Knowledge Base. Significance of each pathway was assessed using the Fisher's exact tests ($P\leq0.05$). Z-score of below (inhibited) or above (activated) 2 is considered as significant.

Culture Medium and Antibodies

Human cells were cultured in X-VIVO-15 (Lonza, Belgium). Flow cytometric analysis was performed using the following antibodies: anti-human CD3 (SK7), anti-human CD3 (UCHT1), anti-human CD4 (RPA-T4), anti-human CD8 (SK1), anti-human CD14 (M5E2), anti-human CD19 (HIB19), anti-human CD25 (M-A251), all from BD Pharmingen, anti-human CD8 (BW 135/80, Miltenyi Biotec), Fluorokine® biotinylated human Interleukin-6 (R&D systems). Cell viability during flow cytometric analysis was determined using 7-AAD and eFluor506 (eBioscience). For blockade experiments, cultures were supplemented with neutralizing antibody against anti-IL-6R (Tocilizumab), PKB/c-Akt VIII inhibitor (Calbiochem), PPARA antagonists (GW6471, Tocris, 0.05 µM) or PPARA agonists (GW7646, Tocris, 0.01 µM) together with IL-6 (100 ng/ml or 1000 IU/ml; CellGenix).

Flow Cytometry and FACS Sort

For surface staining of PBMC or T-cells indicated antibodies were incubated for 30 min at 4° C. and washed twice with PBS. Stained cells were measured on LSRII with FACS Diva Software (BD Bioscience). To detect phosphorylated PKB/c-Akt (anti-Akt, pS473, BD Phosflow), cells were fixed at 37° C. (BD Cytofix™ Buffer); permeabilized (BD™ Phosflow Perm Buffer) washed twice with BD Pharmingen™ stain buffer and stained for the indicated antibody according to manufacturer's instructions.

Isolation of T-Cell Subsets

CD4$^+$CD25$^+$Foxp3$^+$ Treg were isolated from PBMC using anti-CD25 MicroBeads (Miltenyi Biotec) and depleted of contaminating CD8$^+$, CD14$^+$ and CD19$^+$ cells with Dynabeads (Invitrogen) as described previously (Jonuleit et al., 2001). Purity was routinely >80%, Treg functionality was ensured in standard suppressor assays. Untouched CD3$^+$ T-cell isolation was performed using pan T cell isolation kit (Miltenyi Biotec) according to manufacturer's instructions. For some experiments PBMC were depleted of CD3 or CD25 using corresponding Dynabeads (1 bead/cell; Invitrogen).

Cytokine Analysis

Treg-depleted PBMC from HC or MS patients were cultured in presence or absence of Treg (ratio 1:1) and stimulated with anti-CD3 mAb (OKT-3). Cytokines in supernatants were measured 72 h after stimulation by Cytometric Bead Array (BD Bioscience) following manufacturer's instructions and analysed by GraphPad Prism 6 (Statcon).

Suppressor Assays

Treg-depleted PBMC ($10^5$ cells) were stimulated with 0.5 µg/ml anti-CD3 mAb (OKT-3) and cultured in presence or absence of different Treg ratios (Treg:T-cells 1:1 to 1:64) (Jonuleit et al., 2001; Kubach et al., 2007). T-cell proliferation was determined on day three of cultures by addition of 37 kBq/well $^3$H-Tdr for additional 16 h. Some experiments were performed by supplementing cultures with neutralizing mAb against anti-IL-6R (30 ng/ml; Tocilizumab; Roacterma; Roche) or supplemented with IL-6 (100 ng/ml or 1000 IU/ml; CellGenix). PKB/c-Akt VIII inhibitor (0.1 µM; Calbiochem, Isozyme-selective, Akt1/2) was added into individual assays. Some experiments were performed by supplementing cultures with PPARA antagonists (GW6471, Tocris, 0.05 µM) or PPARA agonists (GW7646, Tocris, 0.01 µM) together with IL-6 (100 ng/ml or 1000 IU/ml; CellGenix). For flow cytometric analysis of proliferating T-cells Treg-depleted PBMC were washed in warm PBS and stained with 1 µM CFSE and afterwards cocultured with or without Treg (ratio 1:1) and stimulated with 0.5 µg/ml anti-CD3 mAb. Proliferation was assessed on day 3 after excluding dead cells. Analysis was performed on LSRII (BD Bioscience) and evaluated using DIVA software (BD Bioscience).

RT-PCR and qRT-PCR

RNA was extracted from $2 \times 10^6$ cells using Rneasy Kit (Qiagen) according to manufacturer's instructions. cDNA was generated by reverse transcription with Sensiscript RT Kit (Qiagen) and amplified by quantitative RT-PCR (qRT-PCR, 7300 Real Time PCR System (Applied Biosystem) and the QuantiFAST PCR Kit (Qiagen). Relative IL-6 mRNA (QuantiTect Primer, Qiagen) expression levels were normalized to EF1-α or β-Actin. Relative PPARGC1α, IRF8, FGF19, HNF4A, Hdac, RORA mRNA was analyzed with QuantiTect Primer Assay (Qiagen) according to manufacturer's instructions and expression levels were normalized to β-ACT.

Statistical Analysis

Results represent means plus/minus SEM. Statistical significance was determined using unpaired Mann Whitney test relative to HC. P-values of less than 0.05 were considered significant and indicated in the corresponding figures. For some experiments the bonferroni correction was used to counteract the problem of multiple comparisons: p*=p×n.

A) Schematic overview of the experimental setup used for Affymetrix gene chip analysis. B) Volcano plot of stimulatory response genes that are differently expressed in T-cells of HC and MS and that statistically exhibit a two-fold change. C) Pathway analysis of activated T-cells. Upper panel: numbers of upstream regulators predicted to be activated in activated T-cells of MS, HC or both. Lower panel: numbers of upstream regulators predicted to be inhibited in activated T-cells of MS patients, HC or both. D) Upstream regulators that were statistically more than +1 or −1 (in z-score) significant were examined regarding a connection to the IL-6/PKB/c-Akt signalling pathway (A: Regulator increases production/activity of IL-6/Akt; B: Regulator decreases production/activity of IL-6/Akt; C: Regulator's activity/expression is increased by IL6/Akt, D: Regulator's activity/expression is decreased by IL-6/Akt and E: no information.

CD4$^+$ or CD8$^+$ T-cells from MS patients (red) or HC (black) were left unstimulated or were activated with plate-bound anti-CD3 and anti-CD28 mAb. Expression levels of FGF19, HNF4A, Hdac, RORA, IRF8 and PPARGC mRNA were detected by qRT-PCR. β-Actin was used as housekeeping gene. Four independent experiments are shown as median with interquartile range, p-values relative to HC T-cells. B) Total T-cells (left panel) or either CD4$^+$ or CD8$^+$ T-cells (right panel) from MS patients (red) or HC (black) were left unstimulated or were activated with plate-bound anti-CD3 and anti-CD28 mAb. Expression levels of PPARGC1A mRNA were detected by qRT-PCR. β-Actin was used as housekeeping gene. Six to eleven independent experiments are shown as median with interquartile range, p-values relative to HC T-cells. Left: shown are expression levels of PPARGC1A in activated CD4$^+$ and CD8$^+$ T-cells normalized to resting T-cells. Right: shown are expression levels of PPARGC1A in resting CD3$^+$ T-cells normalized to the housekeeping gene β-Actin.

A) Upper panel: CD3$^+$ T-cells and Treg were coculture in presence (grey) or absence (black) of IL-6 and stimulated with anti-CD3 mAb. Proliferation was determined by $^3$H-Tdr incorporation on day three and displayed as mean±SEM of triplicate measurements. One of four independent experiments is shown. Lower panel: PBMC from HC were cultured for 24 h with (grey) or without (black) IL-6, washed extensively and CD4$^+$ or CD8$^+$ T-cells were isolated. Cells were left unstimulated or were activated with plate-bound anti-CD3 and anti-CD28 mAb for four hours. Shown are expression levels of (PPARGC1A) PGC-1α mRNA in activated CD4$^+$ and CD8$^+$ T-cells (TC) normalized to resting T-cells. β-Actin used as housekeeping gene. Bars represent mean of four experiments, p-values relative to TC without IL-6. B) PKB/c-Akt phosphorylation was analyzed by flow cytometry within CD3$^+$ T-cells after 24 h of culture with (black) or without IL-6 (grey). C) Flow cytometric determination of PKB/c-Akt phosphorylation. T-cells from HC were incubated for 24 h in presence (grey) or absence of IL-6 (black) or in the presence of IL-6 and IL-6R mAb (grey, white striped). Shown is the mean fluorescence intensity (MFI) of pPKB/c-Akt in T-cells, one representative result of five independent experiments. D) PBMC from HC were cultured for 24 h in presence of IL-6 (grey) or in presence of IL-6 and VIII inhibitor (striped, 0.01, 0.1 and 1 µM). PKB/c-Akt phosphorylation was analyzed by flow cytometry within CD3+ T-cells. Shown are the arithmetic means of MFI values including the standard deviation of one representative experiment (n=6).

A) PBMC from HC were cultured for 24 h with media (black), PPARα antagonist (blue) or PPARα agonist (green), washed extensively and expression level of PGC-1α mRNA in activated T-cells was detected by qRT-PCR. β-Actin used as housekeeping gene. Bars represent mean of PGC-1α expression of three different experiments. B) PKB/c-Akt phosphorylation was analysed by flow cytometry within CD3+ T-cells after 24 h of culture with media (black), PPARα agonist (green) or PPARα antagonist (blue). Shown is one representative of four independent experiments. C) T-cells and Treg were coculture in presence (grey) or absence (black) of IL-6 or in presence of IL-6 and PPARα agonist (green) and stimulated with anti-CD3 mAb. Proliferation was determined by $^3$H-Tdr incorporation on day three and displayed as mean±SEM of triplicate measurements. One of three independent experiments is shown. D) T-cells and Treg were coculture in presence (blue) or absence (black) of PPARα antagonist and stimulated with anti-CD3 mAb. Proliferation was determined by $^3$H-Tdr incorporation on day three and displayed as mean±SEM of triplicate measurements. One of three independent experiments is shown.

A) Treg-depleted PBMC from therapy-naïve (black), IFN-β-treated MS patients (blue) or HC (white) were cocultured with allogeneic Treg and stimulated with anti-CD3 mAb. T cell proliferation was determined by 3H-Tdr incorporation on day three. Box plots show percentage of suppression in presence of Treg (ratio 1:1) normalized to proliferation of PBMC alone as median with interquartile range (n=15), P-values relative to suppression of HC or therapy-naïve MS, to avoid familywise error rate bonferroni correction was used indicated as (p*). B) PKB/c-Akt phosphorylation was determined by flow cytometry within CD3+ T-cells from therapy-naïve (red), IFN-βtreated MS patients (blue) or HC (black). Grey histogram depicts isotypic control of MS. Lower panel shows MFI of PKB/c-Akt phosphorylation of six different experiments, p-values relative to MFI of MS. C) IL-6R expression within PBMC from HC (black), therapy-naïve (red), or IFN-β-treated (blue) MS patients was determined by flow cytometry. Box plots show percentage of IL-6R+ cells within CD3+ T-cells of six independent donors, p-values relative to IL-6R expression of therapy-naïve MS or HC are shown. D) CD3+ T-cells from therapy-naïve, IFN-β-treated MS patients, or HC were left unstimulated or were activated for 4 h with plate-bound anti-CD3 and anti-CD28 mAb. Expression level of PGC-1α mRNA in activated T-cells was detected by qRT-PCR. β-Actin was used as housekeeping gene. Six independent experiments are shown as median with interquartile range (n=6), p-values relative to expression level of HC or therapy-naïve MS TC are shown, to avoid familywise error rate bonferroni correction was used indicated as p*.

The invention claimed is:

1. A method for treating a regulatory T-cell (Treg)-resistance-associated autoimmune condition or disease by identifying an agonist that can up-regulate peroxisome proliferator-activated receptor gamma coactivator 1-alpha, PPARGC1A (PGC-1α) in activated T-cells isolated from a patient suffering from the Treg-resistance-associated autoimmune condition or disease, by determination of responsiveness of effector CD4+ and/or effector CD8+ T-cells to Treg, in the patient comprising (i) isolating effector CD4+ and/or effector CD8+ T-cells from blood samples of a patient suffering from the Treg-resistance-associated autoimmune condition or disease, and Treg-sensitive healthy individuals as controls, (ii) activating the effector CD4+ and/or effector CD8+ T-cells with anti-CD3 and/or CD28 antibodies, (iii) measuring the expression levels of PGC-1α in the activated effector CD4+ and/or effector CD8+ T-cells, (iv) comparing the expression levels of PGC-1α of the activated effector CD4+ and/or effector CD8+ T-cells of the patient suffering from the Treg-resistance-associated autoimmune condition or disease with the PGC-1α expression levels in the activated effector CD4+ and/or effector CD8+ T-cells of Treg-sensitive healthy individuals to determine Treg resistance, wherein said agonist is identified by inducing an upregulation of PGC-1α within the effector CD4+ and/or effector CD8+ T-cells of the patient suffering from the Treg-resistance-associated autoimmune condition or disease, and (v) administering said agonist to the patient to treat the Treg-resistance-associated autoimmune condition or disease by normalizing PGC-1α expression and restoring Treg responsiveness in the effector CD4+ and/or effector CD8+ T-cells of said patient.

2. The method according to claim 1, wherein Treg responsiveness of T-cells is restored by normalizing PGC-1a expression in the activated Treg-resistant T-cells of said patient suffering from the Treg-resistance-associated autoimmune condition or disease by administering IFN-β.

3. The method according to claim 1, wherein in addition to PGC-1α, the expression levels of the upstream regulators of Treg-resistant T-cells HNF4A, Hdac, RORA, ESRRA, LPIN1 are determined within CD4+ T-cells and compared to Treg-sensitive T-cells.

4. The method according to claim 1, wherein step (i) includes isolating said CD4+ and/or CD8+ T-cells from peripheral blood mononuclear cells (PBMCs) from said blood samples of said patient suffering from the Treg-resistance-associated autoimmune condition or disease.

* * * * *